United States Patent [19]

Schouteeten et al.

[11] 4,385,006

[45] May 24, 1983

[54] PROCESS FOR PREPARING AROMATIC NITRILES

[75] Inventors: Alain Schouteeten, Ezanville; Yani Christidis, Paris, both of France

[73] Assignee: 501 Societe Francaise Hoechst, France

[21] Appl. No.: 367,125

[22] Filed: Apr. 9, 1982

[30] Foreign Application Priority Data

Apr. 15, 1981 [FR] France ................................ 81 07575

[51] Int. Cl.$^3$ ........................................... C07C 120/08
[52] U.S. Cl. ................................................. 260/465 B
[58] Field of Search ..................................... 260/465 B

[56] References Cited

U.S. PATENT DOCUMENTS 3,287,393 11/1966 Akerstrom ...................... 260/465 B
3,948,968 4/1976 Duke .............................. 260/465 B

*Primary Examiner*—Dolph H. Torrence
*Attorney, Agent, or Firm*—Karl W. Flocks

[57] ABSTRACT

The invention relates to obtaining aromatic nitriles of general formula: $(R)_n$—$C_6H_4$—CN, where n=1, 2 or 3, and the rest R, identical or different represent an atom of hydrogen, chlorine or bromine or an alkyl, aryl, alkoxy, alkylamino, hydroxy or amino group, by a process comprising decarboxylating ammoxidation reaction, in an alkaline aqueous medium, at a pH higher than, or equal to, 13, in the presence of a catalyst based on one or several transition metals and an alkaline hydroxide, applied to an arylglyoxylic acid free or salified, of the formula: $(R)_n$—$C_6H_4$—CO—COOH (where n and R have the above-mentioned meanings), or to one of its functional derivatives of the lactone, lactame or $C_1$-$C_3$-alkyl ester type.

10 Claims, No Drawings

PROCESS FOR PREPARING AROMATIC NITRILES

This invention relates to a novel process for obtaining aromatic nitriles by decarboxylating ammoxidation of arylglyoxylic acids.

Aromatic nitriles are interesting products in organic synthesis and more particularly, the p-hydroxybenzonitrile intervenes for the preparation of 4-hydroxy-3,5-dibromo-benzonitrile and of 4-hydroxy-3,5-diiodo-benzonitrile which are remarkable herbicides.

It is known since the works of GARELLI, Gazzetta, 1890, 20, 697, that arylglyoxylic acids permit access to lower benzonitriles by simultaneous decarboxylation and dehydration of their intermediary oximes. This transformation is generally realized in two steps, i.e. the preparation of the α-hydroxyimino-arylacetic acid by condensing a mineral salt of hydroxylamine with aryl glyoxylic acid, followed most of the time by a treatment with acetic anhydride. In spite of the usual good yields of such reactions, this process has the disadvantage of requiring the use of an expensive reactive, i.e. hydroxylamine.

The ammoxidation reaction has been widely used for several years to have access to aromatic nitriles either starting from alkyl benzenes (B. V. SUVOROV et Al., Zhur.Priklad.Khim., 1963, 36, 1837–52) possibly substituted by halogens (German patent application No. DE OS 1 189 976) or by an alkoxy group (French Pat. No. 2 102 736), either starting from aromatic aldehydes or benzylic primary alcohols (W. BRACKMAN et Al., Rec.Trav.Chim., 1963, 82, 757–62). Recently, the Japanese patent application KOKAI No. 54 145632 teaches how to obtain o-hydroxy-benzonitriles by ammoxidation of o-hydroxymandelic acids, in an aqueous alkaline medium. These processes, however, either require high temperatures above 100° C., or imply anhydrous media, or are limited to particular structures.

The Applicant has now discovered a novel process for obtaining aromatic nitriles of the following general formula:

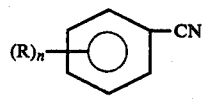

in which n is equal to 1, 2 or 3, and the rests R are identical or different, and each represents an atom of hydrogen or of chlorine or of bromine or an alkyl, aryl, alkoxy, hydroxy, amino, alkylamino group by decarboxylating ammoxidation reaction, in an aqueous alkaline medium, of an aryl glyoxylic acid, free or salified, of the general formula:

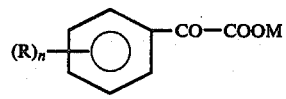

in which R and n keep the above-mentioned meanings and M represents a hydrogen atom, or an alkaline metal.

The process in accordance with this invention is also characterized in that the decarboxylating ammoxidation reaction is carried out:

in liquid phase, in an aqueous alkaline medium, at a pH higher than, or equal to, 13;

in the presence of a strong base, such as sodium hydroxide or potassium hydroxide, in excess relative to the required stoichiometry for salifying the carboxylic and phenolic acid function (possibly functions) present on the starting acid;

at a temperature lower than, or equal to, 120° C.;

under a pressure lower than, or equal to, 11 bars;

in the presence of a catalyst based on a transition metal such as iron, nickel, cobalt and advantageously, copper.

The process in accordance with this invention is easily realized industrially and permits to obtain with good yields aromatic nitriles of the above general formula.

The aryl glyoxylic acid in salified form of the above-mentioned formula can be prepared in situ in the reactional medium from one of its functional derivatives, by alkaline hydrolysis of a lactone such as 2,3-benzofuranedione, possibly substituted on the ring, or of a lactame such as isatine possibly substituted on the ring, and/or alkylated on nitrogen or finally, of a $C_1$–$C_3$-alkyl ester of an arylglyoxylic acid, easily obtained by oxalylation reaction of an aromatic ring.

In an illustrative manner, among the benzonitriles accessible through this process, there can be cited benzonitrile, p-hydroxybenzonitrile, 4-hydroxy-3-methoxybenzonitrile, 3-chloro-4-hydroxybenzonitrile, o-aminobenzonitrile.

The process according to the invention is realized in liquid phase, in an aqueous alkaline medium at a pH higher than, or equal to, 13. In some cases, when the starting product is little soluble in alkaline water, it might be necessary to add thereto a water-miscible solvent such as a $C_1$–$C_3$-alkanol or dioxane to obtain a solution.

The process according to the invention is put into practice in the presence of a strong base such as sodium hydroxide or potassium hydroxide. It is necessary for this strong base to be present in excess relative to the required stoichiometry for salifying the carboxylic and phenolic acid function(s) present on the starting acid.

Usually, such excess is comprised between 10 and 50% of the theoretical quantity necessary for salifying the acid function(s) present on the starting acid and preferably such excess is comprised between 25 and 50% of the theoretical quantity.

The ammoxidation agent consists of a mixture of ammonia and oxygen in varied proportions. Such mixture which is always in excess relative to the stoichiometry of the ammoxidation reaction can be diluted with an inert gas. Since the process is carried out in aqueous phase, it is particularly interesting to effect the reaction with a great excess of concentrated aqueous ammonia solution containing from 28 to 34 g of ammonia dissolved in 100 g of the solution. The molar ratio ammonia/oxygen can be different from that corresponding to the reaction stoichiometry.

Since oxygen is little soluble in water, the reaction is usually effected under agitation and with an oxygen or oxygen-containing gas pressure higher than the ambient pressure. Advantageously, the reaction is effected with a pressure lower than, or equal to, 11 bars.

The process according to the invention is usually carried out at a temperature lower than, or equal to, 120° C. and advantageously between 100° and 120° C. The reactional durations vary according to various factors, i.e. the structure of the starting product, the agitation speed, the pressure, the catalyst concentration and the like, and they may vary within a wide range but are generally of between 1 and 4 hours.

The process is carried out in the presence of a catalyst based on one or more transition metals such as iron, cobalt, nickel, copper.

Advantageously, the catalyst is constituted by cupric, ferric, cobaltic ions and/or nickel II, alone or mixed, and they are introduced directly into the reactional medium, adding a mineral or organic salt of these metals such as the pentahydrated cupric sulfate, the ferric chloride, the tetrahydrated cobalt II acetate, the tetrahydrated nickel II acetate. Preferably, the catalyst is constituted by pentahydrated cupric sulfate.

This catalyst can be used at very different concentrations but usually the catalyst concentrations expressed in atoms/grams of metal per mole of starting acid are comprised between 0.001 and 0.1, and preferably, between 0.01 and 0.1.

The carbonic anhydride formed during the reaction is converted in situ as its formation develops into alkaline carbonate. It does not interfere with the progress of the reaction.

The aromatic nitriles obtained can be isolated from the reactional medium by any known means, in particular, by extraction with a water-immiscible organic solvent. If necessary, they be purified thereafter by known means such as recrystallization, distillation, and the like.

As was stated before, the aromatic nitriles easily obtained by the novel process are products which are much used industrially, more particularly, the p-hydroxybenzonitrile serves for the preparation of 4-hydroxy-3,5-diiodo-benzonitrile and 4-hydroxy-3,5-dibromo-benzonitrile, which are remarkable herbicides.

The following examples are given to illustrate but not to limit the invention.

EXAMPLE 1

A solution of 15.4 g (0.1 mole) of 97% phenylglyoxylic acid, 150 g (3 moles) of 34% pure ammonia solution, 1.75 g (0.007 mole) of pentahydrated cupric sulfate and 6 g (0.15 mole) of sodium hydroxide in pellets are heated for 1 hour at 100° C. in an oxygen atmosphere, under agitation, and with a total pressure of 8 bars. Thereafter, after cooling to the ambient temperature, the reaction medium is filtered, thereby isolating 1.05 g (0.0086 mole) of benzamide, M.p.=128°–129° C. The alkaline filtrate is thereafter submitted to repeated extractions with ether.

The organic phases being united, washed with water up to neutrality of the washings, then dry concentrated under vacuum, supply a crystallized mixture (3.3 g) of benzonitrile and benzamide, the relative proportions of which as determined by chromatography in gaseous phase, are 60% of benzonitrile and 40% of benzamide.

EXAMPLE 2

A solution of 112 g (0.5 mole) of sodium parahydroxy-phenylglyoxylate crystallized with two molecules of water, 750 g (15 moles) of 34% pure ammonia solution, 30 g (0.75 mole) of sodium hydroxide in pellets, and 9 g (0.036 mole) of pentahydrated cupric sulfate in solution in 161.5 g of water, is heated for 4 hours at 100° C., in an oxygen atmosphere, under agitation, and under a total pressure of 8 bars.

After cooling to the ambient temperature, the reactional medium is acidified to pH=5, with diluted sulfuric acid, and then is submitted to repeated extractions with ethyl acetate. The organic phases being united, washed with water, dried, filtered and dry concentrated under vacuum, leave 49.5 g (0.416 mole) of parahydroxy-benzonitrile. M.p.=110°–113° C.

EXAMPLE 3

A solution of 13.4 g (0.068 mole) of 4-hydroxy-3-methoxy-phenyl-glyoxylic acid, 102 g (2.04 mole) of 34% pure ammonia solution, 1.2 g (0.005 mole) of pentahydrated cupric sulfate, 6.8 g (0.17 mole) of sodium hydroxide in pellets and 22 g of water, is heated for 4 hours at 100° C. in an oxygen atmosphere under agitation, and with a total pressure of 8 bars.

Thereafter, the reactional medium is treated as in example 2. Thus, there is isolated 3.75 g (0.025 mole) of 4-hydroxy-3-methoxybenzonitrile having after recrystallization a melting point of 88° C.

EXAMPLE 4

A solution of 13.7 g (0.068 mole) of 3-chloro-4-hydroxy-phenyl-glyoxylic acid, 102 g (2.04 moles) of 34% pure ammonia solution, 1.2 g (0.005 mole) of pentahydrated cupric sulfate, 6.8 g (0.17 mole) of sodium hydroxide in pellets, and 22 g of water, is heated for 4 hours at 100° C., in an oxygen atmosphere, under agitation, and with a total pressure of 8 bars.

Thereafter, the reactional medium is treated as in Example 2.

There is thus isolated 7.75 g (0.05 mole) of 3-chloro-4-hydroxybenzonitrile having, after recrystallization, a melting point of 155° C.

EXAMPLE 5

A solution of 112 g (0.5 mole) of sodium p-hydroxyphenylglyoxylate, crystallized with two molecules of water, 30 g (0.75 mole) of sodium hydroxide in pellets, 9 g (0.036 mole) of tetrahydrated cobalt II acetate, 750 g (15 moles) of 34% pure ammonia solution in 161.5 g of water, is heated for 2 hours at 120° C., in an oxygen atmosphere, under agitation and with a total pressure of 11 bars.

Thereafter, the reactional medium is treated as in Example 2. Thus, there is isolated 37.5 g of p-hydroxybenzonitrile containing 3.4 g of p-hydroxybenzamide after chromatographic analysis in gaseous phase. The p-hydroxy-benzonitrile is purified by distillation under vacuum, B.p.:=148±2° C.

EXAMPLE 6

A solution of 112 g (0.5 mole) of sodium-p-hydroxyphenylglyoxylate crystallized with two molecules of water, 30 g (0.75 mole) of sodium hydroxide, 9.7 g (0.036 mole) of hexahydrated ferric chloride, 750 g (15 moles) of 34% pure ammonia solution in 161.5 g of water, is heated for 2 hours at 120° C. in an oxygen atmosphere under agitation, and with a total pressure of 11 bars.

Thereafter, the reactional medium is treated as in Example 2.

Thus, there is isolated 31 g of p-hydroxy-benzonitrile containing 4 g of p-hydroxybenzamide which is purified by distillation under vacuum. B.p.=148±2° C.

EXAMPLE 7

A mixture of 73.6 g (0.5 mole) of isatine, 30 g (0.75 mole) of sodium hydroxide in pellets, 9 g (0.036 mole) of pentahydrated cupric sulfate, 750 g (15 moles) of 34% pure ammonia solution in 161.5 g of water is heated for 120 minutes, at 100° C., in an oxygen atmosphere, under agitation, and with a total pressure of 8 bars.

Thereafter, the cooled reaction medium is submitted to successive extractions with ether. The ether phases being united, are washed with water, dried, filtered and dry concentrated under vacuum. There is thus isolated 34 g of o-aminobenzonitrile containing 50% of o-aminobenzamide. The desired nitrile is thereafter purified by distillation: B.p.=267°–268° C.

It will be understood that this invention was only described in an explanatory but not limitative manner and that any useful modification thereto for substituting equivalents can be effected without however departing from its scope as defined in the appended claims.

We claim:

1. A process for obtaining aromatic nitriles of the general formula I:

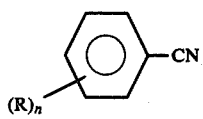

(in which n is equal to: 1, 2 or 3, and the rests R, whether identical or different, are selected from the group comprising the atoms of hydrogen, chlorine and bromine and the alkyl, aryl, alkoxy, alkylamino, hydroxy and amino groups), by the decarboxylating ammoxidation reaction, in an aqueous alkaline medium, of a compound selected from the group comprising an arylglyoxylic acid, free or salified, of general formula II:

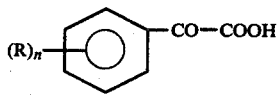

(in which n and R have the same meanings as above), and of a functional derivative of such acid selected from the group comprising a 2,3-benzofuranedione, an isatine and an alkyl arylglyoxylate at a pH higher than, or equal to, 13, in the presence of a catalyst based on at least one transition metal, and an alkaline metal hydroxide.

2. A process according to claim 1, wherein the functional derivative is a 2,3-benzofuranedione of the general formula III:

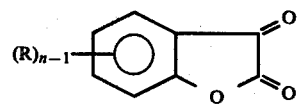

(in which R and n have the same meanings as in claim 1).

3. A process according to claim 1, wherein the functional derivative is an isatine of the general formula IV:

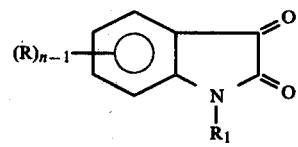

in which R and n have the same meanings as in claim 1, and $R_1$ is selected from the hydrogen atoms and the alkyl groups.

4. A process according to claim 1, wherein the functional derivative is an alkyl arylglyoxylate of the general formula V:

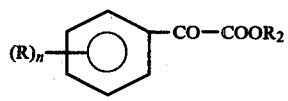

in which R and n have the same meanings as in claim 1, and $R_2$ is a $C_1$–$C_3$-alkyl group.

5. A process according to claim 1, wherein the salified arylglyoxylic acid is the aryl-glyoxylate of an alkaline metal selected from the group comprising sodium.

6. A process according to claim 1, wherein the catalyst is based on at least one metal selected from the group comprising copper, iron, nickel and cobalt.

7. A process according to claim 6, wherein the reaction is carried out in liquid phase at a temperature equal to, or lower than, 120° C., with a pressure lower than, or equal to, 11 bars, and in the presence of cupric ions.

8. A process according to claim 6, wherein the reaction is carried out in the liquid phase at a temperature lower than, or equal to, 100° C., with a pressure lower than, or equal to, 10 bars and in the presence of ferric ions.

9. A process according to claim 6, wherein the reaction is carried out in liquid phase at a temperature lower than, or equal to, 120° C., under a pressure lower than, or equal to, 11 bars, and in the presence of cobalt II ions.

10. A process according to claim 6, wherein the reaction is carried out in liquid phase at a temperature lower than, or equal to, 120° C., under a pressure lower than, or equal to, 11 bars, and in the presence of nickel II ions.

* * * * *